United States Patent

Eimers et al.

[11] 4,323,501
[45] Apr. 6, 1982

[54] ESTERS OF PHOSPHOROUS ACID

[75] Inventors: Erich Eimers, Krefeld; Dieter Margotte, Krefeld-Bookum; Helmut Schmid, Krefeld; Rolf Dhein, Krefeld-Bookum, all of Fed. Rep. of Germany

[73] Assignee: Bayer Aktiengesellschaft, Leverkusen, Fed. Rep. of Germany

[21] Appl. No.: 843,186

[22] Filed: Oct. 18, 1977

Related U.S. Application Data

[60] Division of Ser. No. 635,010, Nov. 25, 1975, Pat. No. 4,073,769, which is a continuation of Ser. No. 409,503, Oct. 25, 1973, abandoned, which is a continuation-in-part of Ser. No. 278,909, Aug. 9, 1972, Pat. No. 3,794,629.

[30] Foreign Application Priority Data

Aug. 11, 1971 [DE] Fed. Rep. of Germany ....... 2140207
Nov. 14, 1972 [DE] Fed. Rep. of Germany ....... 2255639

[51] Int. Cl.$^3$ .............................................. C07F 9/145
[52] U.S. Cl. ................................................... 260/333
[58] Field of Search ......................................... 260/333

[56] References Cited

U.S. PATENT DOCUMENTS 3,209,013 9/1965 Hechenbleikner et al. ......... 260/333
3,794,629 2/1974 Eimers et al. ........................ 260/333

FOREIGN PATENT DOCUMENTS 2255639 5/1974 Fed. Rep. of Germany.

Primary Examiner—Norma S. Milestone
Attorney, Agent, or Firm—Gene Harsh; Lawrence S. Pope

[57] ABSTRACT

Phosphites of the general formula:

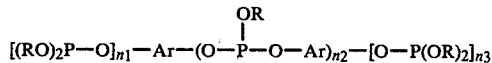

in which
$n_1$ is an integer;
$n_2$ is 0 or an integer;
$n_3$ is an integer;
at least one of the groups R is an oxetane group as hereinafter defined or a hydrocarbon radical being substituted at least by one oxetane group as hereinafter defined;
the remaining groups R are selected from alkyl, aralkyl, cycloalkyl, aryl and hetaryl groups; and
the group or groups Ar are the same or different at-least-divalent aromatic groups the free valencies of which are directly linked to the aromatic nuclei; and
a process for their preparation.

14 Claims, No Drawings

ESTERS OF PHOSPHOROUS ACID

CROSS REFERENCE TO RELATED APPLICATIONS

This is a division of application Ser. No. 635,010 filed Nov. 25, 1975 now U.S. Pat. No. 4,073,769 which is a continuation of application Ser. No. 409,503 filed Oct. 25, 1973, now abandoned, which application itself is a continuation-in-part of application Ser. No. 278,909, filed Aug. 9, 1972, now U.S. Pat. No. 3,794,629.

BACKGROUND OF THE INVENTION

This invention relates to new polyesters of phosphorous acid, hereinafter referred to as phosphites, to their production, and to their use as stabilizers for polycarbonates.

In copending application, Ser. No. 278,909, now U.S. Pat. No. 3,794,629 there are described aromatic polycarbonates stabilized against discoloration after exposure to heat by the addition thereto of a neutral ester of phosphorus acid having at least one oxetane group.

SUMMARY AND DETAILED DESCRIPTION OF THE INVENTION

A new class of neutral esters of phosphorus acid, according to the invention, which contain at least one oxetane group and at least one residue of an at-least-dihydric phenol per molecule have also been found to be effective in stabilizing polycarbonates against discoloration by heat.

The new esters of the invention, hereinafter referred to as phosphites, which contain at least one oxetane group and at least one residue of an at-least-dihydric phenol per molecule are of the general formula:

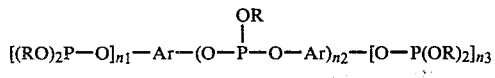

(I)

in which
- $n_1$ is an integer; preferably 1 to 9; especiall preferred 1 to 4;
- $n_2$ is 0 or an integer; preferably 0, 1 and 2; especially preferred 0;
- $n_3$ is an integer; preferably 1 to 9; especially preferred 1 to 4;

at least one of the groups R is an oxetane group as hereinafter defined or a hydrocarbon radical being substituted at least by one oxetane group as hereinafter defined;

the remaining groups R are selected from alkyl, aralkyl, cycloalkyl, aryl and hetaryl groups; and the group or groups Ar are the same or different at-least-divalent aromatic groups the free valencies of which are directly linked to the aromatic nuclei.

The oxetane group, as referred to in this specification, is the heterocyclic group:

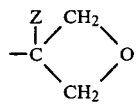

in which Z is a hydrogen, $C_1$–$C_{16}$-alkyl, $C_1$–$C_4$-alkoxy, $C_7$–$C_{10}$-aralkyl, alkoxyalkyl having 2-18 carbon atoms or aryloxyalkyl radical having 7-16 carbon atoms, such as, for example, —$CH_3$, —$C_2H_5$, —$OC_2H_5$, —(n)$C_5H_{11}$, —$CH_2C_6H_5$, —$CH_2.O.C_6H_5$ and —$CH_2.O.C_2H_5$. For brevity the oxetane group is sometimes referred to hereinafter as Ox.

The radical R can itself be an oxetane radical, e.g. when Z=H.

Examples of suitable radicals R not carrying oxetane radicals, which are derived from monohydroxy compounds R—OH, are alkyl radicals having 1 to 18 carbon atoms, monocyclic and polycyclic cycloalkyl radicals having 3 to 10 carbon atoms, phenylalkyl radicals having 7 or 8 carbon atoms, mono- and poly-nuclear aryl radicals having 6 to 18 carbon atoms, (such as phenyl, naphthyl, anthracyl, phenanthryl, biphenyl, phenoxyphenyl and fluorenyl radicals), and the tetrahydrofuryl radical. When R is an aryl radical it may carry substituents, for example, alkyl and halogen radicals, and especially alkyl radicals having up to nine carbon atoms, chlorine and bromine radicals.

The radical R being substituted by at least one oxetane group is derived from $C_1$–$C_{18}$ monoalcohols being substituted by one or more oxetane groups. An example of a suitable hydrocarbon radical R which carries an oxetane group in the phosphites defined above is the methyl radical being substituted by one oxetane group:

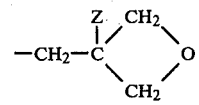

Examples of suitable at-least-divalent aromatic radicals Ar are the radicals derived from the following at-least-dihydric phenols by elimination of the hydroxyl groups: hydroquinone; resorcinol; pyrocatechol; di-t-butyl-pyrocatechol; 4,4'-dihydroxydiphenyl; bis-(hydroxyphenyl)-alkanes such as $C_1$–$C_8$-alkylene-bis-phenols or $C_2$–$C_8$-alkylidene-bisphenols; bis-(hydroxyphenyl)-cycloalkanes such as $C_5$–$C_{15}$-cycloalkylene-bisphenols or $C_5$–$C_{15}$-cycloalkylidene-bisphenols; α,α'-bis-(hydroxyphenyl)-diisopropylbenzenes such as α,α'-bis-(4-hydroxyphenyl)-p-diisopropyl-benzene; dihydroxy-naphthalenes; dihydroxyanthracenes; phloroglucinol and pyrogallol. The corresponding nuclear-alkylated or nuclear-halogenated compounds may also be used, for example, bis-(4-hydroxyphenyl)-propane-2,2 (bisphenol A); bis-(4-hydroxy-3,5-dichlorophenyl)-propane-2,2 (tetrachlorobisphenol A); bis-(4-hydroxy-3,5,-dibromophenyl)-propane-2,2 (tetrabromobisphenol A); bis-(4-hydroxy-3,5,-dimethyl-phenyl)-propane-2,2 (tetramethylbisphenol A; bis-(4-hydroxy-3-methyl-phenyl)-propane-2,2; and bis-(4-hydroxyphenyl)-cyclohexane-1,1 (bisphenol Z).

The compounds of the invention prove to be effective stabilizers, for example, for aromatic polycarbonates, and are superior to the known stabilizers. They do not show the increased browning of polycarbonates on heat treatment which is to be observed with ordinary phosphites not containing oxetane groups.

Of the compounds claimed, the compounds of the formula (I) which are derived from 2,2-bis(hydroxyphenyl)-alkanes and monoalcohols containing oxetane groups are preferred, that is to say compounds of the formula (I) wherein Ar corresponds to a radical of the formula II,

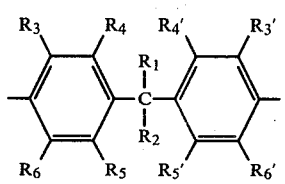
(II)

wherein
- R₁ and R₂ are identical or different radicals selected from hydrogen atoms, alkyl groups having up to 18 carbon atoms, mono- and poly-cyclic cycloalkyl groups having 3 to 6 carbon atoms, and mono- and polycyclic aryl groups having 6 to 18 carbon atoms; and
- R₃, R₃', R₄, R₄', R₅, R₅', R₆ and R₆' are identical or different radicals selected from hydrogen atoms, alkyl groups having up to 18 carbon atoms, mono- and polycyclic cycloalkyl groups having 3 to 6 carbon atoms, mono- and polycyclic aryl groups having 6 to 18 carbon atoms, alkoxy groups having 1 to 18 carbon atoms, aryloxy groups having up to 18 carbon atoms, and halogen atoms. The alkyl substituents which are suitable as substituents in II may be unbranched or branched and saturated or unsaturated. Suitable aryl substituents may be, for example, phenyl or biphenyl, and preferred halogen substituents are Cl or Br.

The compounds of the formula I in which Ar corresponds to a radical of the formula II are obtained by reaction of the corresponding bisphenols of the formula III;

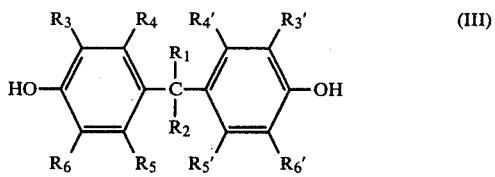
(III)

wherein
R₁ to R₆ and R₃' to R₆' are defined as in II, in the manner described below.

The phosphites of the invention are high-boiling liquids, resins or solids. They are readily soluble in organic solvents, especially in the solvents used in the manufacture of polycarbonates, and are therefore particularly suitable for use as stabilizers in polycarbonates of high viscosity which are manufactured and/or processed at high temperatures.

The new phosphites, some examples of which are listed below, may be manufactured, and used, individually or as mixtures. The phosphites may be of linear or branched structure.

A selection of examples provides the following survey:

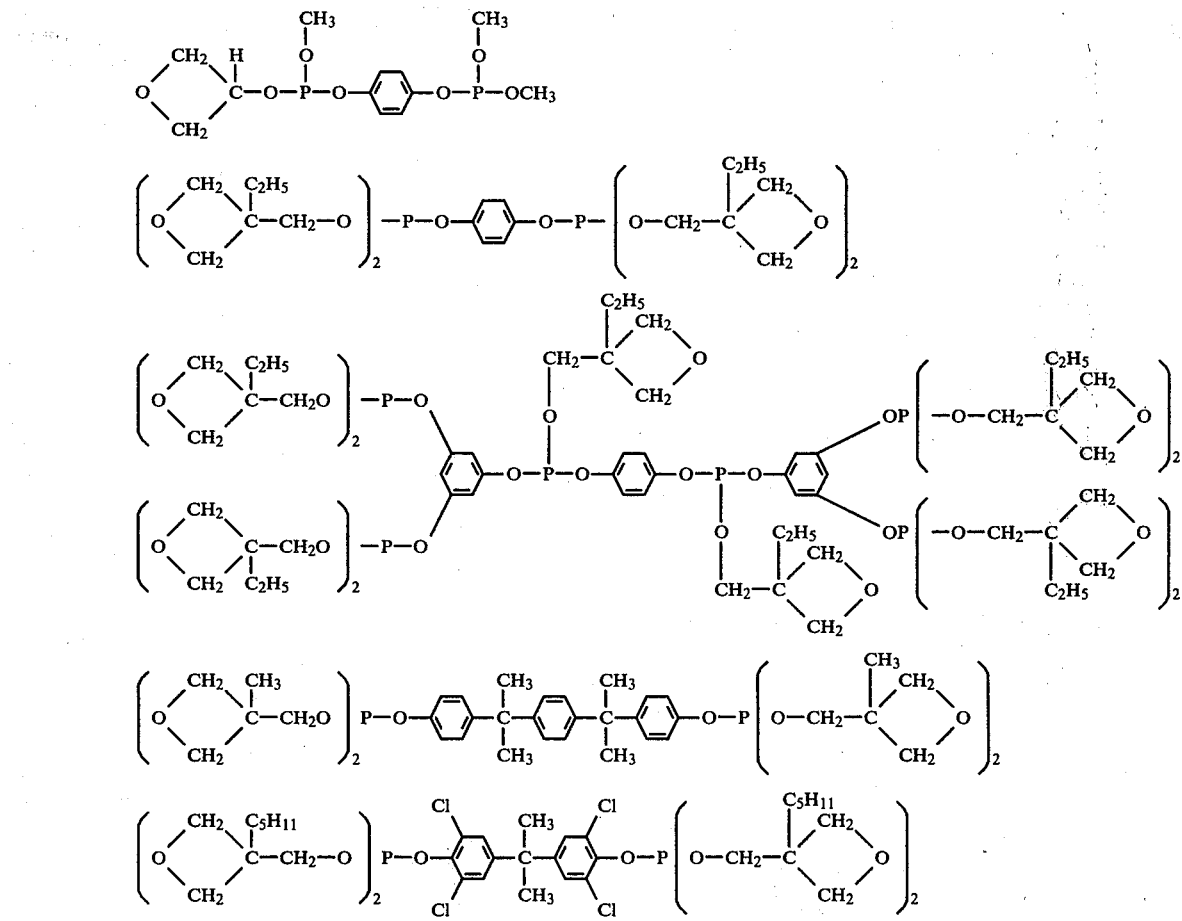

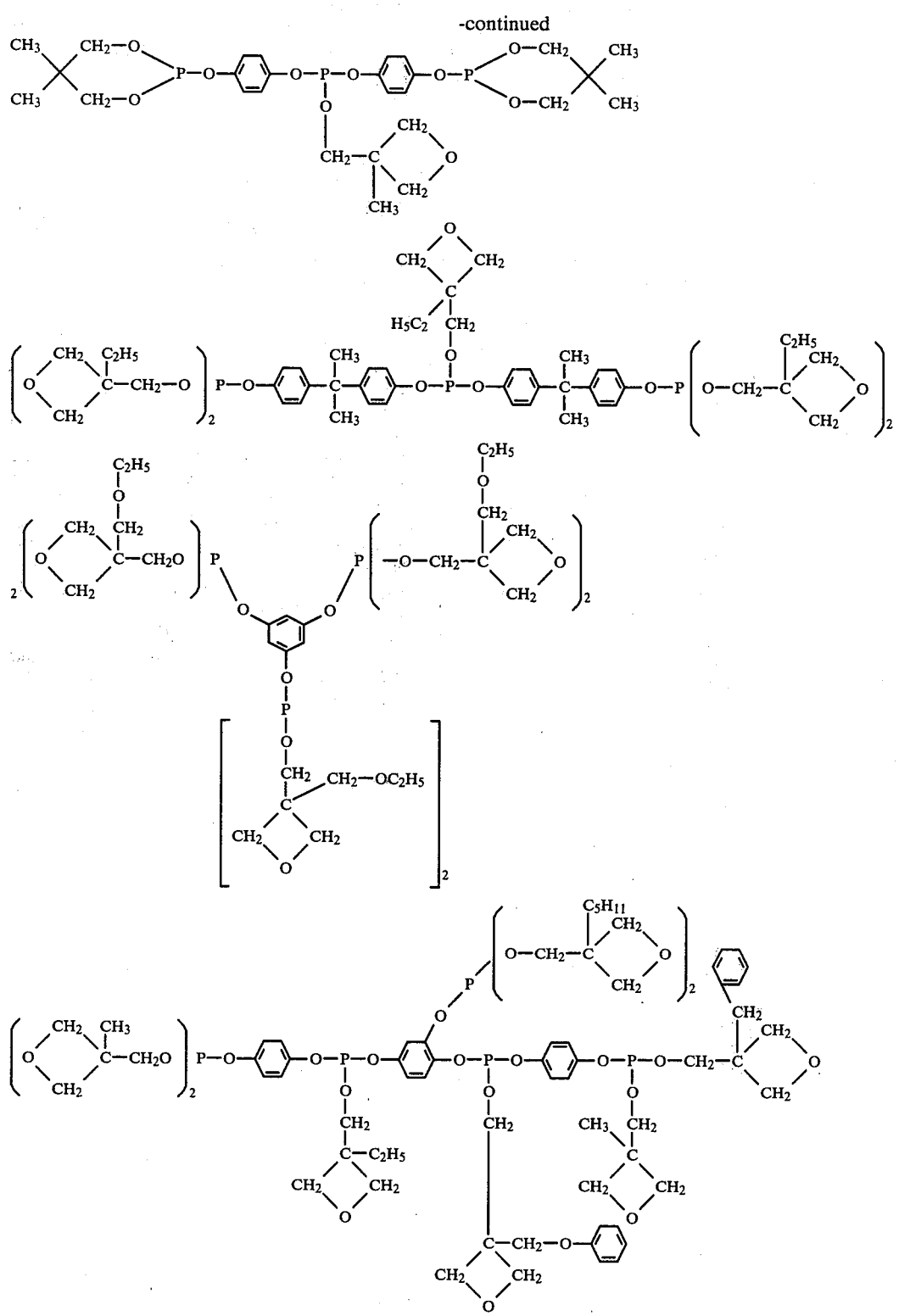

The invention also provides a process for the production of the phosphites of the invention, in which process one or more at-least-dihydric phenols (as required to provide the groups Ar), preferably a bisphenol of the general formula III given above, the triphenylphosphite are reacted together, either in succession or simultaneously, with one or more monoalcohols of the general formula R—OH (as required to provide the groups R) in the presence of a basic catalyst. Phenol is eliminated during the reaction.

The reaction is preferably carried out at 100°–180° C. Preferred basic catalysts, which are preferably present in an amount of 0.01 to 1 wt. % based on the triphenylphosphite, include sodium, potassium, sodium and potassium hydroxides and carbonates, alkali metal (especially sodium) methylates and phenolates, alkali metal borohydrides, alkali metal borates, and tributylamine.

The reaction may be carried out in bulk or with the addition of solvents. The molar ratio of the reactants, namely monoalcohol R-OH containing oxetane groups, aryl compound and triphenylphosphite, follows from the end product of the formula I which is to be manufactured, with the proviso that in the one-stage reaction process the oxetane groups containing monoalcohol R—OH is preferably used in a slight excess of up to 20% referred to the theoretical amount being necessary.

In a preferred form of the process of the invention one mole of an aryl compound containing 2 phenolic hydroxyl groups, especially a bisphenol of the general formula III given above, is reacted with about two moles of triphenylphosphite in the presence of a basic catalyst with the elimination of two moles of phenol, and the resulting product (a mixed aryl-phenyl phosphite) is then reacted with a monoalcohol of the general formula R—OH [in which R is a hydrocarbon radical containing up to 18 carbon atoms and being substituted by an oxetane group], the molar amount R—OH being equivalent to the amount of phenol to be eliminated, to produce the desired phosphite. This process is to be preferred if the speed of replacement of phenol by aryl compound containing hydroxyl groups, on the one hand, differs very greatly from the speed of replacement of phenol by mono-alcohol containing oxetane groups, on the other hand. Such is the case, for example, when using o-substituted bisphenols such as tetramethylbisphenol A, as the aryl component. The process is illustrated below:

tertiary amines, sodium hydroxide, sodium acetate, and sodium bicarbonate. Here again the reaction may be carried out in two stages if the speed of reaction of the reactants differs, for example:

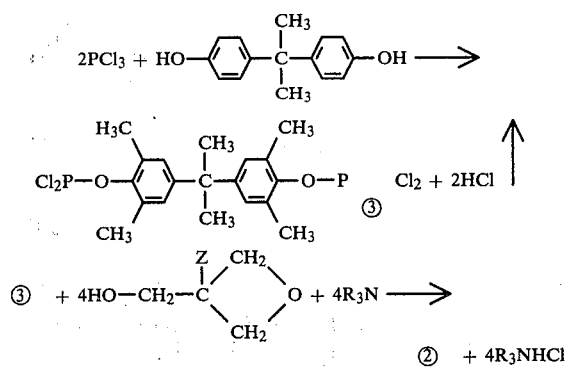

Suitable reaction temperatures are between −10° and +80° C. and the reaction may be carried out in bulk or in the presence of solvents.

Examples of monoalcohols R—OH being substituted by oxetane groups suitable for the manufacture of the compounds of the formula I are 3-hydroxymethyl-oxetane, 3-ethoxymethyl-3-hydroxymethyl-oxetane, 3-phenoxymethyl-3-hydroxymethyl-oxetane, 3-ethyl-3-hydroxymethyloxetane, 3-n-pentyl-3-hydroxymethyloxetane, 3-methyl-3-hydroxymethyloxetane and 3-benzyl-3-hydroxymethyl-oxetane.

3-Hydroxy-oxetane may be mentioned as an example

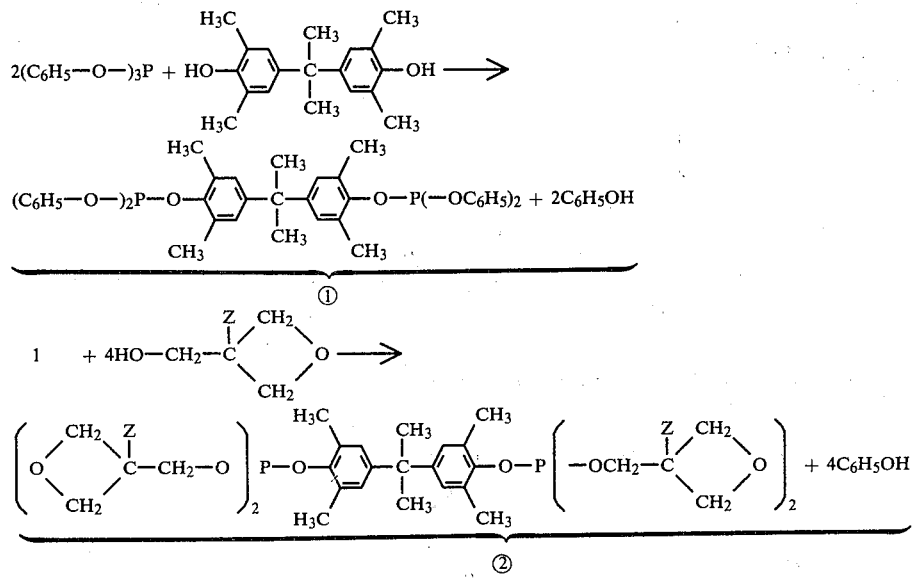

What has been said above with regard to reaction temperature, catalysis and reaction medium also applies to this two-stage process.

The invention also provides a further method for the production of the phosphites of the invention in which at least one at-least-dihydric phenol (as required to provide the desired groups Ar) is reacted with phosphorous trichloride and, either simultaneously or subsequently, with at least one alcohol R—OH (as required to provide the desired groups R) in the presence of a stoichiometric amount of a hydrogen chloride acceptor. Suitable hydrogen chloride acceptors are for example of a compound R—OH in which R corresponds to the oxetane group Ox.

To produce phosphites of the invention in which R is an oxetane group, oxetanes containing hydroxyl groups, Ox—OH are used as the alcohols R—OH in the process described above.

To manufacture the compounds according to the invention, of the formula I, it is furthermore possible to employ, according to the processes described above, monohydroxy compounds R—OH which are free of oxetane groups, such as monoalcohols or monophenols, in a manner which is in itself known together with the monoalcohols R—OH containing oxetane groups and/or oxetanes Ox—OH containing hydroxyl groups; suitable monohydroxy compounds R—OH free of oxetane groups are, for example, decyl alcohol, stearyl alcohol, benzyl alcohol, phenol, p-chlorophenol, p-nonylphenol, 2,6-dimethylphenol, 2,6-di-t-butylphenol, p-t-butylphenol, 2,4,6-trichlorophenol, p-hydroxydiphenyl, o-hydroxydiphenyl ether and mixtures of these compounds.

Preferred solvents, especially for the manufacture of the compounds of the formula I when starting from phosphorus trichloride, are those in which the chlorides produced as by-products are insoluble. Such solvents are for example, chloroform, carbon tetrachloride or toluene. Tertiary amines which may be used as HCl acceptors in the manufacturing process starting from phosphorus trichlorides are, for example, triethylamine, tributylamine, trimethylamine, N,N-dimethylaniline, N,N-diethylaniline and pyridine.

As stated above, the invention relates also to the use of the phosphites of the invention as stabilizers for polycarbonates.

The invention therefore provides a plastics material comprising a polycarbonate based on at least one aromatic dihydroxy compound and at least one phosphite of the invention.

Possible polycarbonates to be stabilized according to the invention are the polycondensates obtainable according to known processes by reaction of dihydroxydiarylalkanes with phosgene or diesters of carbonic acid, and in addition to the unsubstituted dihydroxydiarylalkanes, those whereof the aryl radicals carry methyl groups or halogen atoms in the o-position and/or m-position to the hydroxyl group are also suitable. Equally, branched polycarbonates are suitable.

The polycarbonates to be stabilized have average molecular weights of between 10,000 and 100,000, preferably between 20,000 and 40,000.

Suitable aromatic dihydroxy compounds are, for example, hydroquinone; resorcinol; 4,4'-dihydroxydiphenyl; bis-(hydroxyphenyl)alkanes such as, for example, $C_1$–$C_8$-alkylene-bisphenols or $C_2$–$C_8$-alkylidene-bisphenols; bis-(hydroxy-phenyl)-cycloalkanes such as, for example, $C_5$–$C_{15}$-cycloalkylene-bisphenols or $C_5$–$C_{15}$-cycloalkylidenebisphenols; bis-(hydroxy-phenyl)-sulphides; -ethers; -ketones; -sulphoxides or -sulphones; and also $\alpha,\alpha'$-bis-(hydroxyphenyl)-diisopropylbenzene as well as the corresponding nuclear-alkylated or nuclear-halogenated compounds. Preferred polycarbonates are those based on bis-(4-hydroxyphenyl)-propane-2,2 (bisphenol A); bis-(4-hydroxy-3,5-dichloro-phenyl)-propane-2,2 (tetrachlorobisphenol A); bis-(4-hydroxy-3,5-dibromophenyl)propane-2,2 (tetrabromobisphenol A); bis-(4-hydroxy-3,5-dimethyl-phenyl)propane-2,2 (tetramethylbisphenol A); bis-(4-hydroxy-3-methylphenyl)propane-2,2; bis-(4-hydroxy-phenyl)-cyclohexane-1,1 (bisphenol Z) and on trinuclear bisphenols such as $\alpha,\alpha'$-bis-(4-hydroxyphenyl)-p-diisopropylbenzene.

Further bisphenols suitable for the manufacture of polycarbonate are described in U.S. Pat. Nos. 3,028,365, 2,999,835, 3,148,172, 3,271,368, 2,970,137, 2,991,273, 3,271,367, 3,280,078, 3,014,891 and 2,999,846 and in German patent applications No. P 2,063,050, P 2,063,052, P 2,211,957, and P 2,211,956.

The new phosphites containing oxetane groups, of the formula I, can be added to the polycarbonates to be stabilized either individually or in combination with one another, in concentrations of between 0.01 and 0.2% by weight, preferably in concentrations of between 0.025 and 0.1% by weight, calculated relative to the total weight of the polycarbonate and stabilizer.

The plastics material of the invention can be manufactured by either adding the phosphite in the pure form to the fused polycarbonate or optionally adding it as a solution in a low-boiling solvent to the polycarbonate solution. The polycarbonates claimed, which are stabilized against discoloration, can also be manufactured by impregnating the powdered or granulated polycarbonate with the phosphite (or, if appropriate, with its solution in a solvent) in a suitable mixing apparatus. The plastics material is then worked-up in accordance with known techniques.

Corresponding remarks apply to the addition of the phosphite during the manufacture of the polycarbonate according to known methods, in the melt or in a solvent.

The plastics material according to the invention can furthermore contain known additives such as, for example, fillers, dyestuffs, pigments and/or other stabilizers without the action of the added phosphites containing oxetane groups being influenced thereby.

The new phosphites can also be employed for the stabilization of mixtures containing brominated polycarbonate, in combination with barium carbonate, strontium carbonate or calcium carbonate, in accordance with U.S. Pat. No. 3,733,296.

The polycarbonates stabilized according to the invention are particularly used where the moldings manufactured are exposed to a prolonged high heat and also for all articles for which high light transmission is demanded. This applies preferentially to use in the lighting field, for example for lamp covers or glazing with polycarbonate sheets.

EXAMPLES

Manufacture of the polycarbonate used for the stabilization tests

Approximately 454 parts of 4,4'-dihydroxydiphenyl-2,2-propane and 9.5 parts of p-tert.-butylphenol are suspended in 1.5 l of water. The oxygen is removed from the reaction mixture, in a 3-neck flask equipped with stirrer and gas inlet tube, by passing nitrogen through the reaction mixture for 15 minutes, while stirring. 355 parts of 45% strength sodium hydroxide solution and 1,000 parts of methylene chloride are then added. The mixture is cooled to 25° C. 237 parts of phosgene are added over a period of 120 minutes while maintaining this temperature by cooling. An additional amount of 75 parts of a 45% strength sodium hydroxide solution is added after 15–30 minutes or after the absorption of phosgene has started. 1.6 parts of triethylamine are added to the resulting solution and the mixture is stirred for a further 15 minutes. A highly viscous solution is obtained, of which the viscosity is regulated by adding methylene chloride. The aqueous phase is separated off. The organic phase is washed with water until free of salt and alkali. The polycarbonate is isolated from the washed solution and dried. The polycarbonate has a relative viscosity of 1.29–1.30 measured in an 0.5% strength solution in methylene chloride at 20° C. This corresponds roughly to a molecular weight of 32,000. The polycarbonate thus obtained is extruded and granulated.

Examples of the manufacture of the phosphorous acid esters claimed according to the invention. Temperatures are °C. unless otherwise indicated.

EXAMPLE 1

310 g (1 mol) of triphenylphosphite, 114 g of bisphenol A (0.5 mol), 255 g (2.38 mols) of ethyl-3-hydroxymethyl-oxetane and 1 g of sodium methylate are heated to 120° C. over the course of 1 hour in an apparatus equipped with a stirrer and distillation column and are kept at this temperature for 1 hour. A waterpump vacuum is then applied and 232 g of phenol are distilled off through the column over the course of 4 hours at a sump temperature which is slowly raised to 165° and a head temperature of 85°–88°. The column is then removed and a high vacuum is applied. A further 60 g of a distillate consisting of a mixture of phenol and oxetane are distilled off under a pressure of 0.1 mm Hg and at a sump temperature raised to 190°. 385 g of a syrupy brownish residue are left. 0.85 g of phosphoric acid is added to this resinous product. The product is then again heated under a vacuum of 0.1 mm Hg to a temperature of 238°, in the course of which a further 93 g of distillate pass over. 290 g of a colorless opalescent resin are obtained as the residue.

Analysis: Found. C 62–62.2%; H 7.41%; P 8.2–8.3%. Calculated.(+) C 62.6; H 7.75; P 8.3.

+ for

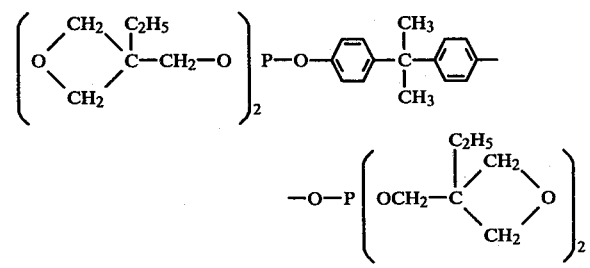

EXAMPLE 2

320 g of triphenylphosphite (approx. 1 mol), 142 g of tetramethylbisphenol (0.5 mol) (4,4'-bis-hydroxy-3,5,3',5'-tetramethyldiphenylol-2,2-propane) and 3 g of sodium phenolate are initially introduced into the same apparatus as in Example 1, heated to 120° and kept at 120° for 3 hours. A waterpump vacuum is then applied and 90 g=95.7% of theory of phenol are distilled off over the course of 8 hours while slowly raising the temperature to 175° and at a pressure of 8 mm Hg. 255 g of 3-ethyl-3-hydroxymethyloxetane and 1.5 g of sodium phenolate are then added and the mixture is kept for 1½ hours at 120°. A waterpump vacuum is then again applied and 150 g of a distillate containing predominantly phenol are stripped off through a column over the course of 4 hours while slowly raising the temperature to 180°. 10 g of glacial acetic acid are then added to neutralize the sodium phenolate and the mixture is again partially distilled in a high vacuum at 2 mm Hg. Over the course of 1 hour, a further 60 g of distillate pass over at a head temperature of 65°–175° and a sump temperature of 110°–210°. 285 g of a light yellow-colored transparent resin are obtained.

Analysis: Found. C 64.2–4%; H 8.25%; P 7.55%. Calculated(+) C 64.2; H 8.22; P 7.22.

(+)for

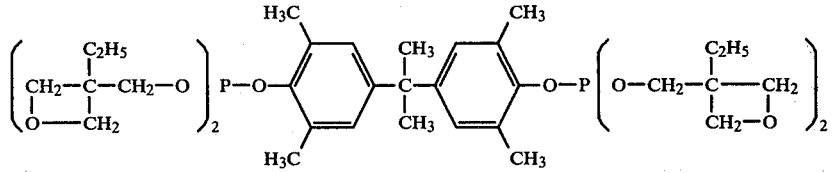

MANUFACTURE OF THE STABILIZED POLYCARBONATE COMPOSITIONS

The granulated polycarbonate manufactured in accordance with the above description is mixed with the phosphites, the manufacture of which has been described above, by so-called tumbler coating. Since the phosphites mentioned are of resinous consistency, they were applied to the polycarbonate not in their pure form but in the form of an approx. 3% strength solution in methylene chloride, to achieve better mixing with the polycarbonate. The granules treated in this way are extruded at 300° in a mixing screw to give a ribbon. This ribbon is again chopped up to give granules which are converted into standard test rods in an injection molding machine at 330°.

HEAT-AGEING

The test specimens manufactured in the manner described above were heat-treated at 140° in a drying cabinet. The light transmission was measured with the aid of a spectrophotometer. The decrease in the light transmission at 420 nm over the course of the heat treatment in each case serves as a measure of the increasing browning of the test specimen (see table).

As can be seen from the data in the table which follows, the stabilizing action of the aryl-modified phosphites claimed corresponds to the stabilizers of application Ser. No. 278,909.

The relative viscosity of the polycarbonates stabilized according to the invention showed no reduction compared to the viscosity of the phosphite-free polycarbonate. Accordingly, no degradation of the polycarbonate molecule has taken place due to the stabilizer.

| Light transmission (*) of the polycarbonate test rods at 420 nm and a layer thickness of 4 mm, after treatment at 140° | | | | | |
|---|---|---|---|---|---|
| | Amount of | Heat treatment | | | |
| Polycarbonate Test Rod | stabilizer added, % | 0 days | 6 days | 12 days | 21 days |
| without additive | none | 81.0 | 80.3 | 80.1 | 79.0 |
| phosphite (x) | 0.05 | 82.0 | 80.4 | 79.2 | 75.0 |
| phosphite according to the invention, from Example 1 | 0.1 | 84.0 | 82.0 | 81.0 | 80.5 |
| phosphite according to the | | | | | |

-continued

| Polycarbonate Test Rod | Amount of stabilizer added, % | Heat treatment | | | |
|---|---|---|---|---|---|
| | | 0 days | 6 days | 12 days | 21 days |
| invention, from Example 2 | 0.1 | 84.0 | 83.0 | 81.5 | 80.5 |

Light transmission (*) of the polycarbonate test rods at 420 nm and a layer thickness of 4 mm, after treatment at 140°

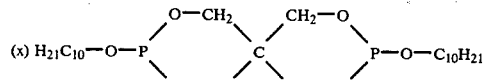

(*) measured according to DIN 5,033 and DIN 4,646

EXAMPLE 3
Manufacture of the phosphite:

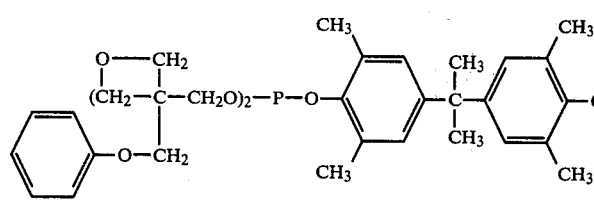

21.8 g of 3,3',5,5'-tetramethylbisphenol, 47.6 g of triphenylphosphite and 0.4 g of sodium methylate are heated to 120° C. under nitrogen and kept at 120° C. for 1 hour. A vacuum is then applied and 13.2 g of phenol are distilled off over the course of 2¼ hours at a pressure of 10 mm Hg. In the course thereof, the heating temperature is raised to 183° C. The reaction mixture is then cooled and 60.0 g of phenoxymethylhydroxymethyloxetane are added. The mixture is then heated to 182° C. over the course of a few hours, under a waterpump vacuum, in the course of which 28.5 g of phenol distill off. 2 ml of glacial acetic acid are added to neutralize the sodium methylate. Finally the reaction mixture is further heated to 220° C. in a high vacuum. In the course thereof, a further 13 g of a liquid distillate pass over.

Analysis: Found. C 68.3-4%; H 6.84%; P 5.45-50%. Calculated. 67.8; 6.63; 5.56.

EXAMPLE 4
Manufacture of the phosphite:

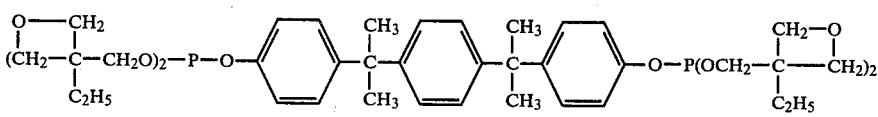

310 g of triphenylphosphite, 173 g of α,α'-bis-(4-hydroxyphenyl)-p-diisopropylbenzene and 2 g of sodium phenolate are fused together and heated at 120° C. for 4 hours. A waterpump vacuum is then applied and 95 g phenol are distilled off under a pressure of 17 mm Hg. The reaction mixture is cooled and 0.5 g of sodium phenolate are added, followed by 255 g of 3-ethyl-3-hydroxymethyloxetane. The reaction vessel is provided with a distillation column and heated to 120° C. over the course of 2 hours. Thereafter a vacuum is applied, whereupon 165 g of a distillate consisting mainly of phenol distill off at a pressure of 23 mm Hg. During the distillation, the temperature was raised to 187° C. Thereafter the column is removed and the reaction product is heated in a high vacuum up to a temperature of 230° C., in the course of which a further 70 g of distillate pass over. The reaction product is a pale yellowish-colored resin.

Analysis: Found. C 67.1-2%; H 8.08%; P 7.15%. Calculated. C 66.5; H 7.85; P 7.16.

EXAMPLE 5
Manufacture of the phosphite:

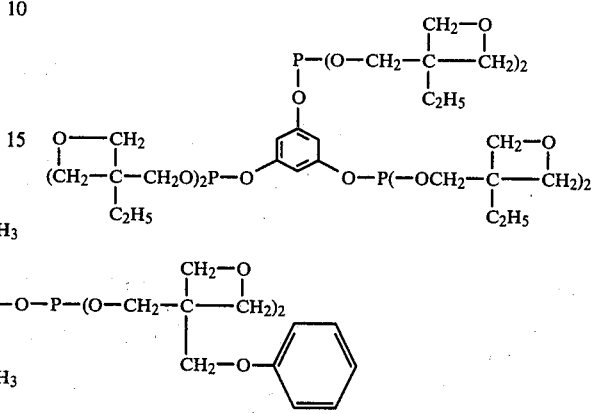

186 g of triphenylphosphite, 25 g of phloroglucinol and 0.5 g of sodium methylate are gradually heated to 120° C., in the course of which the mixture dissolves to give a clear melt. A waterpump vacuum is then applied. 56 g phenol are distilled off while the temperature in the melt is gradually raised to 160° C. The reaction mixture is then cooled and the apparatus is provided with a distillation column. 160 g of hydroxymethylethyloxetane are then added and the mixture is heated to 120° C. for 2 hours. Thereafter vacuum is again applied and 105 g of phenol are distilled off while gradually heating to 182° C. The column is then removed and a further 30 g of a liquid distillate are filtered off while again heating in a high vacuum to 185° C. The reaction product which remains is a yellowish-colored tough resin.

Analysis: Found. C 54.8-9%; H 7.7%; P 10.3%. Calculated. C 55.4; H 7.62; P 10.26.

EXAMPLE 6

310 g of triphenyl phosphite (1 mol), 114 g of bisphenol A (0.5 mol), 294 g of ethyl-3-hydroxymethyl-oxetane and 1 g of sodium methylate are introduced into an apparatus according to Example 1 and heated in one hour to 120° C. A vacuum is applied and the mixture heated up to 165° C. in 3 hours and 233 g of phenol distilled off at a pressure of 23 mm Hg and a head temperature of 90° C. The column is removed and further heated in vacuo to 185° C., 35 g of a mixture consisting of phenol and oxetane alcohol being distilled off. Thereafter 0.85 g of H₃PO₄ are added to the resulting resinous product. Following this the product is slowly heated in high vacuum up to 220° to 240° C. and kept at this temperature until another 196 g have distilled over up to a head temperature of 184° C. A colourless, opaque resin is obtained as residue with the following analytic data: C: 64.7% H: 7.4% P: 8.5% From these data it can be concluded that the product has the following structural formula:

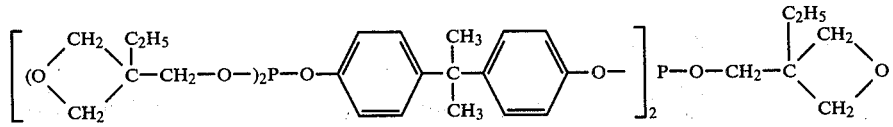

analytic data calculated: C: 64.2% H: 7.4% P: 8.3%

Upon testing the product as a stabilizer it behaves in a similarly favourable manner as the product described in Example 1.

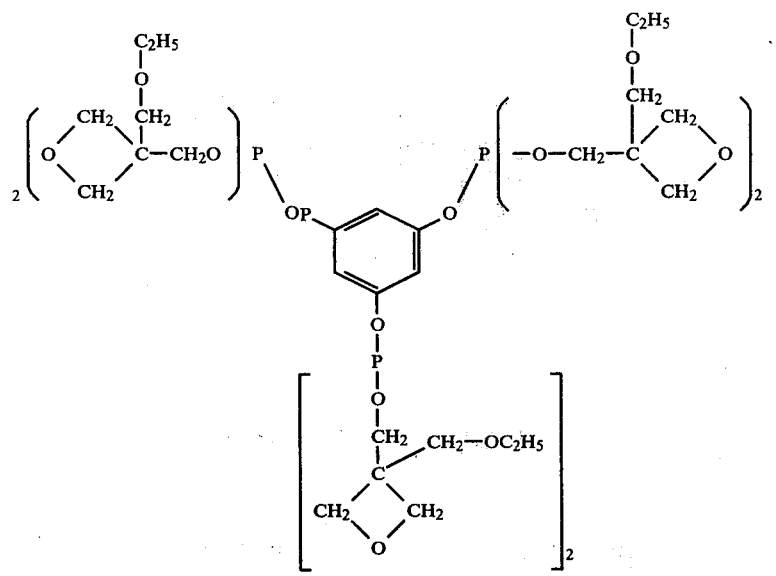
14. A phosphite of the formula:
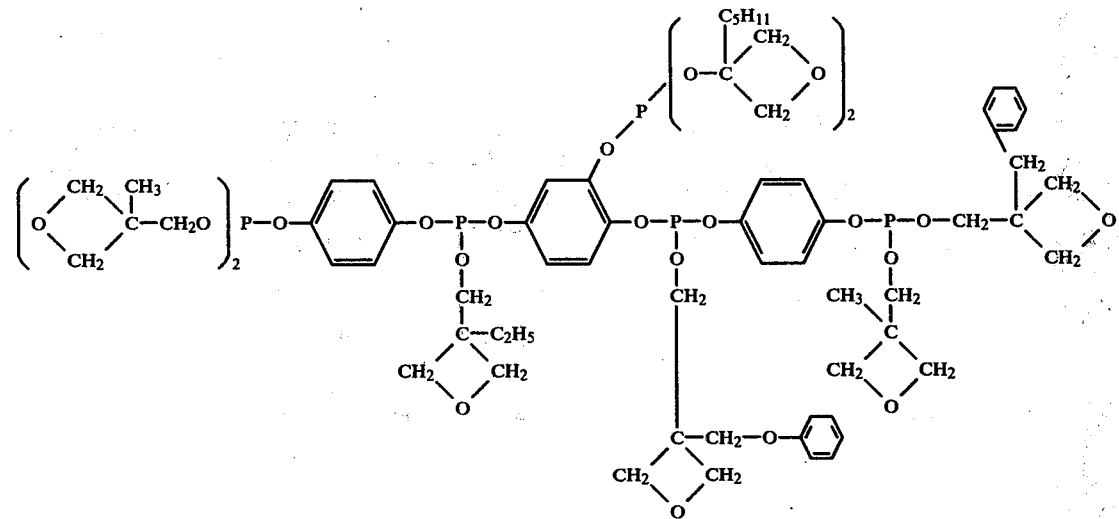

What is claimed is:

1. The phosphite:

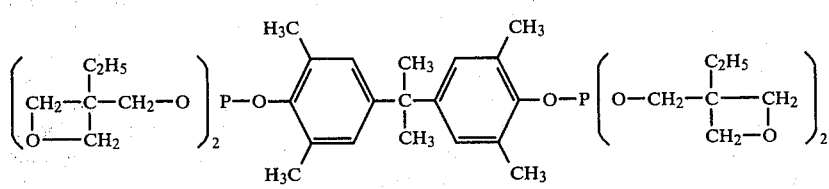

2. The phosphite:

3. The phosphite:

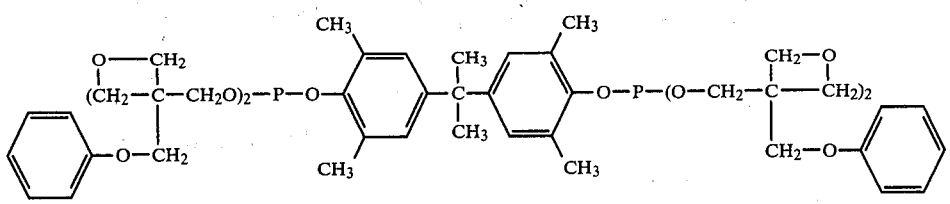

4. The phosphite:

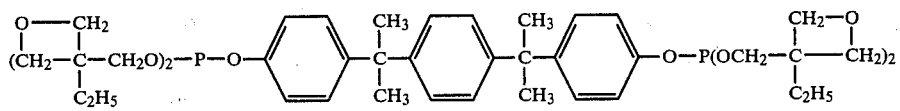

5. The phosphite:

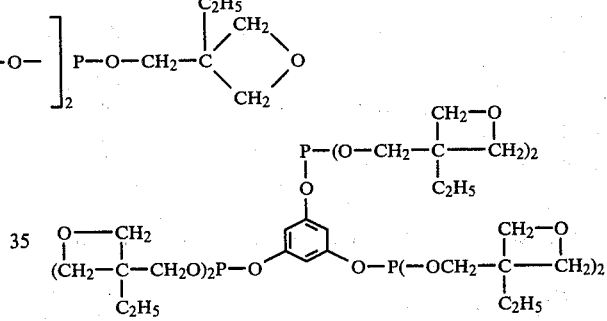

6. A phosphite of the formula:

7. A phosphite of the formula:

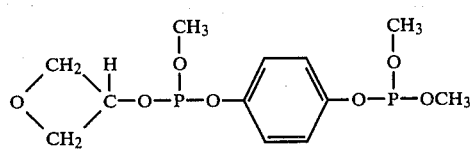

8. A phosphite of the formula:

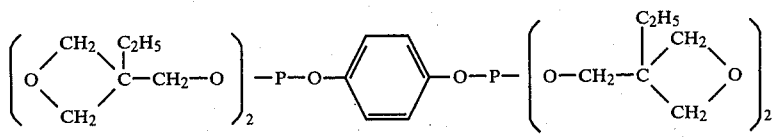

9. A phosphite of the formula:
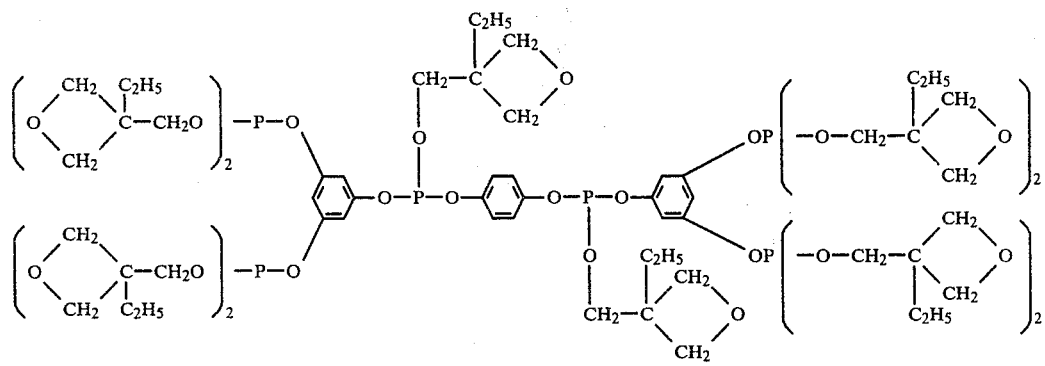
10. A phosphite of the formula:
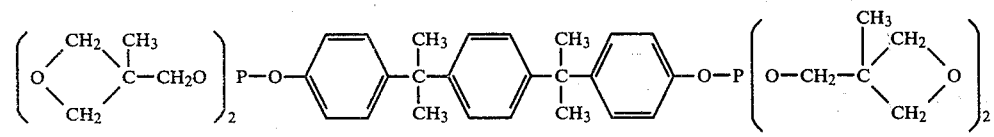
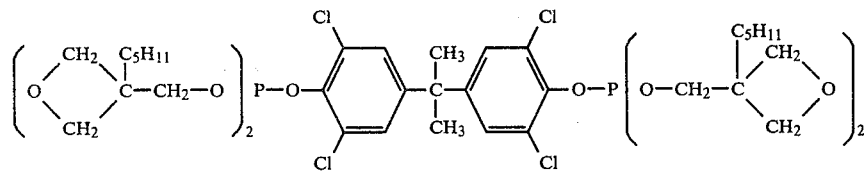
11. A phosphite of the formula:
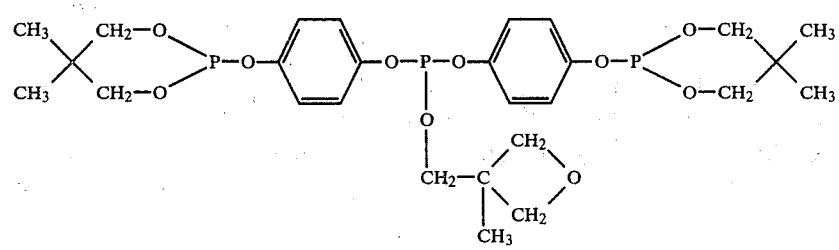
12. A phosphite of the formula:
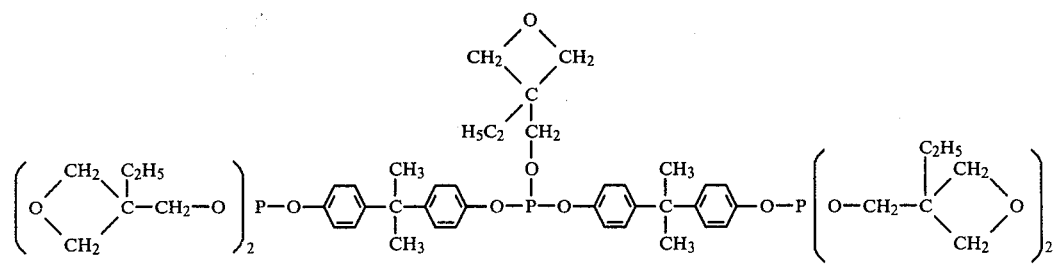
13. A phosphite of the formula: